United States Patent [19]
Peterson

[11] 3,988,145
[45] Oct. 26, 1976

[54] ORGANOTIN COMPOUNDS AS HERBICIDES

[75] Inventor: Donald J. Peterson, Springfield Township, Hamilton County, Ohio

[73] Assignee: The Procter & Gamble Company, Cincinnati, Ohio

[22] Filed: Apr. 3, 1975

[21] Appl. No.: 563,912

Related U.S. Application Data

[60] Division of Ser. No. 368,141, June 8, 1973, Pat. No. 3,897,560, which is a division of Ser. No. 164,941, July 21, 1971, Pat. No. 3,784,580, which is a continuation-in-part of Ser. No. 10,303, Feb. 10, 1970, abandoned.

[52] U.S. Cl. ................................................. 71/97
[51] Int. Cl.$^2$ .......................................... A01N 9/00
[58] Field of Search ........................................ 71/97

[56] References Cited
UNITED STATES PATENTS

| | | | |
|---|---|---|---|
| 3,095,434 | 6/1963 | Stamm et al. | 71/97 |
| 3,264,177 | 8/1966 | Kenaga | 71/97 |
| 3,453,099 | 7/1969 | Popoff et al. | 71/97 |

*Primary Examiner*—Glennon H. Hollrah
*Attorney, Agent, or Firm*—Rose Ann Dabek; Jerry J. Yetter; Richard C. Witte

[57] ABSTRACT

Disclosed are novel organotin compounds and a process for preparing same. These organotin compounds correspond to the general formula:

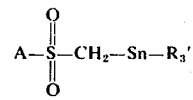

where A is alkyl of from 1 to 14 carbon atoms; aryl; substituted aryl; or R$_2$N-, where each R is alkyl of from 1 to 14 carbon atoms; and each R' is alkyl of from 1 to 14 carbon atoms; or aryl. The organotin compounds of the invention having insecticidal, acaricidal, bacteriostatic, fungicidal and herbicidal properties are employed in the formulation of pesticidal compositions.

11 Claims, No Drawings

ORGANOTIN COMPOUNDS AS HERBICIDES

CROSS REFERENCE TO RELATED APPLICATION

This is a division of application Ser. No. 368,141, filed June 8, 1973, now U.S. Pat. No. 3,897,560, which is a division of Ser. No. 164,941 filed July 21, 1971, now U.S. Pat. No. 3,784,580, which application is a continuation-in-part of copending application Ser. No. 10,303, filed Feb. 10, 1970 now abandoned.

BACKGROUND OF THE INVENTION

This invention relates to novel compounds. More particularly, this invention relates to organotin compounds, a method for their preparation, pesticidal (including herbicidal) compositions containing such compounds and to a method of combating both plant and insect pests.

The desirability of controlling or eradicating insect pests and common disease-causing organisms is clearly accepted. Thus, compounds possessing insecticidal, acaricidal, bacteriostatic and fungicidal properties and especially adapted to such control or eradication are of particular importance.

The necessity of controlling or eradicating undesirable plants, i.e., weeds, from fields planted with growing crops by means of chemical herbicides is also clearly accepted. Such chemical control of undesirable plant growth is more efficient and less expensive than manual control. However, the chemical control of weeds in the presence of growing food crops has been somewhat hindered because of several factors. For example, many herbicides are unsuitable for use with food crops because of toxic residues remaining on the crops after application.

It is an object of the present invention to provide novel organotin compounds and a method for their preparation.

A further object is to provide novel compounds which are useful as insecticides, acaricides, bacteriostats, fungicides and herbicides. Another object is to provide pesticidal (i.e., herbicidal and insecticidal) compositions containing the novel organotin compounds. A still further object is to provide novel compositions and methods effective for combating insects and other pests such as weeds, and bacterial and fungal organisms. Other objects of the invention will be apparent from consideration of the invention described more fully hereinafter.

DETAILED DESCRIPTION OF THE INVENTION

The novel organotin compounds of the present invention are of the formula:

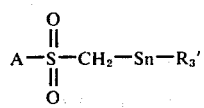

where A is a member selected from the group consisting of alkyl of from 1 to 14 carbon atoms (e.g., methyl, ethyl, n-propyl, iso-propyl, n-butyl, iso-butyl, amyl, iso-amyl, hexyl, n-octyl, n-dodecyl, n-tetradecyl); aryl (e.g., phenyl, naphthyl); substituted-aryl (e.g., p-methoxyphenyl, p-N,N-dimethylaminophenyl, p-chlorophenyl, o-methoxyphenyl); and $R_2N-$, where each R is alkyl of from 1 to 14 carbon atoms; and each R' is alkyl of from 1 to 14 carbon atoms; or aryl.

In a process aspect, this invention comprises reacting an organometallic compound having the formula:

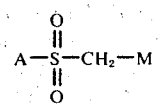

wherein M is alkali metal (e.g., lithium); or MgX with a trihydrocarbyltin halide of the formula $R_3'SnX$ wherein A, and each R' are as defined hereinbefore and X is halide (e.g., chloride, bromide). The reaction of the organometallic compound and trihydrocarbyltin halide proceeds with facility according to the following scheme:

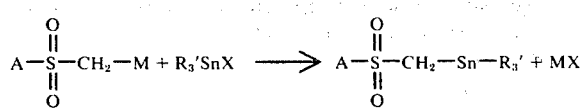

Suitable organometallic reactants of the process of the invention include the (alkylsulfonylmethyl)-lithiums; (arylsulfonylmethyl)lithiums; (substituted-arylsulfonylmethyl)lithiums; (N,N-dialkylamino-sulfonylmethyl)lithiums and the corresponding magnesium halides. Specific examples include (butylsulfonylmethyl)lithium; (N,N-dimethylaminosulfonylmethyl)-lithium; (phenylsulfonylmethyl)lithium; (p-methoxyphenylsulfonylmethyl)lithium; (p-N,N-dimethylaminophenylsulfonylmethyl)lithium; (o-methoxyphenylsulfonyl-methyl)magnesium bromide; (p-chlorophenylsulfonyl-methyl)magnesium bromide.

The process of the present invention is carried out at a temperature of from about −60° C to about 30° C, a preferred temperature being from −10° C to 10° C. Especially suitable herein are proportions of reactants corresponding to about stoichiometric amounts. Examples of suitable trialkyltin halides and triaryltin halides for reaction with the organo-metallic reactants hereinbefore described include trimethyltin chloride, triethyltin chloride, tri-n-propyltin chloride, tri-iso-propyltin chloride, tri-n-butyltin chloride, tri-iso-butyltin chloride, triamyltin chloride, tri-iso-amyltin chloride, tri-n-hexyltin chloride, tri-n-octyltin chloride, tri-n-decyltin chloride, tri-n-dodecyltin chloride, trimethyltin bromide, triphenyltin chloride, triphenyltin bromide, and the like.

Tri-n-butyltin chloride is a preferred trialkyltin halide herein and undergoes the desired reaction with facility. Its ready availability and reaction with (phenylsulfonylmethyl)lithium, for example, to provide (phenylsulfonylmethyl)tributyltin having unique insecticidal and acaricidal properties make the tri-butyltin chloride the trialkyltin halide reactant of choice.

The process of the present invention can be conducted in the presence of non-reactive solvents or diluents. These solvents or diluents should not contain any of the reactive groups contained in the reactive compounds hereinbefore mentioned either as a part of the structure of the solvent or as part of the impurities present in the solvents if maximum yields are desired. The use of solvents which will react with organolithium reactants is also generally undesirable. Suitable non-reactive solvents or diluents are to be found in such classes of compounds as the aliphatic hydrocarbons, aliphatic ethers, cyclic ethers and trialkylamines. Examples of suitable non-reactive hydrocarbon solvents include hexane, petroleum ether and Stoddard solvent. Among the ether compounds which are suitable as solvents are diethylether, dibutyl ether, tetrahydrofuran, 1,2-dimethoxyethane and diethylene glycol dimethyl ether. Amine compounds which can serve as solvents for the reaction include triethylamine and N,N,N',N'-tetramethylethylenediamine. Other similar non-reactive solvents or diluents can be used with substantially equivalent results. Preferred herein is tetrahydrofuran which enables formation of the desired products in high yield and degree of purity. The use of mixtures of two or more non-reactive compounds as the reaction medium is suitable.

The organometallic, e.g., organolithium and organomagnesium halide reactants described hereinbefore, can be readily prepared. Generally, these reactants can be prepared by reaction of a methyl sulfone having the formula:

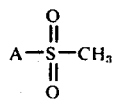

wherein A is as hereinbefore defined with a metalating agent such as alkali metal hydrides (e.g., sodium, potassium and lithium hydride); alkali metal alkyls, wherein the alkyl group contains from 1 to about 6 carbons atoms; alkali metal aryls; and alkylmagnesium halides (e.g., methylmagnesium chloride). Preferred metalating agents include n-butyllithium and methyl-magnesium chloride from the standpoints of their facility of reaction and ready availability. Alkyl-magnesium chlorides are preferred for the metalation of substituted arylmethylsulfones, e.g., p-chlorophenylmethylsulfone, they being preferred as tending to minimize side reactions.

The organolithium and organomagnesium halide reactants of the process of the invention are prepared by reaction with an appropriate metalating agent at a temperature of from −60° C to about 20° C depending on the particular sulfone, metalating agent, solvent and the like. Reactions of methylsulfones with n-butyllithium occur rapidly at room temperature while the corresponding reactions with methylmagnesium halides proceed at moderate to slow rates. Ether and mixed ether-hexane solvents are preferred, respectively, when the alkylmagnesium halide and organolithium metalating agents are employed.

Metalation of sulfones with n-butyllithium, for example, proceeds according to the following scheme:

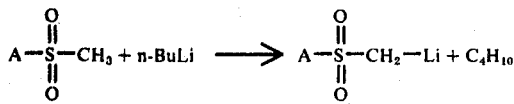

Preparations of organomagnesium halide and organolithium reactants of the process of the invention are described in greater detail by Lamar Field, John R. Holsten and R. Donald Clark, *J. Org. Chem.*, 81, 2572–2578, (1959); and by E. J. Corey and Michael Chaykovsky, *J. Am. Chem. Soc.*, 87:6, 1345–1353, March 20, 1965.

The products and processes of the present invention are described in more detail in the following examples.

EXAMPLE I

A 250-ml, three-necked flask fitted with a stirrer, a dropping funnel, and a thermometer was swept thoroughly with argon and maintained in an air-free condition by a mercury-filled trap. The flask was charged with 27 ml. of tri-n-butyltin chloride dissolved in 50 ml. of tetrahydrofuran (THF). To the solution of tributyltin chloride was added dropwise with stirring 100 ml. of an approximately one-molar solution of (butylsulfonylmethyl)lithium in a hexane-THF mixture. The temperature was held at −10° C to 10° C during the addition which required 15 minutes. The reaction mixture was then agitated by stirring at room temperature for 2 hours. The reaction mixture was hydrolyzed by pouring into aqueous one-molar ammonium chloride. Extraction from the hydrolyzate with ether solvent and purification by distillation yielded the desired product (butylsulfonylmethyl)-tributyltin. The product, a colorless liquid, had a boiling point of 161°–165° C/0.1 mm. Hg. Analysis gave 48.4% Carbon and 9.2% Hydrogen compared to the calculated values, respectively, of 48.0% and 9.0%. Infrared and proton nuclear magnetic resonance spectral analyses confirmed the assigned structure.

Similar results are obtained when the following organotin halides are employed in an equimolar amount in place of tributyltin chloride in that the corresponding (butylsulfonylmethyl)trihydrocarbyltin compounds, respectively, are obtained: trimethyltin chloride; tri-n-octyltin chloride; tri-n-tetradecyltin bromide; triphenyltin bromide.

EXAMPLE II

Employing the apparatus and procedure of Example I, 100 ml. of an approximately one-molar solution of (N,N-dimethylaminosulfonylmethyl)lithium in hexane-THF solvent was added slowly over a period of 30 minutes to 0.1 mole of tri-n-butyltin chloride dissolved in THF. The temperature at addition was −60° C provided by a dry ice-acetone bath and rose through the addition period to 0° C. Following the complete addition, the reaction mixture was stirred for 2 hours at room temperature (20° C) and hydrolyzed by pouring into an aqueous one-molar ammonium chloride solution. Extraction from the hydrolyzate with ether solvent and purification by vacuum distillation yielded the desired compound, (N,N-dimethylaminosulfonylmethyl)tributyltin. The product, a pale-yellow liquid, had a boiling point of from 158°–160° C/0.1 mm. Hg. Analysis gave 43.8% Carbon and 8.5% Hydrogen compared to the calculated values, respectively, of 43.7% and 8.5%. The assigned structure was confirmed by infrared and proton nuclear magnetic resonance spectral analyses.

EXAMPLE III

Using the apparatus and procedure of Example I, 100 ml. of an approximately one-molar solution of (phenylsulfonylmethyl)lithium in hexane-THF solvent was added dropwise with stirring to 0.1 mole of tributyltin chloride dissolved in THF. The temperature was maintained by means of an ice bath in the range of from 0° C to 10° C. Following the complete addition which required one-half hour, the reaction mixture was stirred for 3 hours at room temperature and hydrolyzed by pouring into aqueous one-molar ammonium chloride. Extraction from the hydrolyzate with ether solvent and purification by vacuum distillation yielded an odorless, pale-yellow liquid having a boiling point of 180° C/0.05 mm. Hg. The product, (phenylsulfonylmethyl)-tributyltin was analyzed and gave 51.4% Carbon and 7.9% Hydrogen compared with the calculated values, respectively, of 51.3% and 7.7%. Infrared and proton nuclear magnetic resonance spectral analyses confirmed the assigned structure.

The corresponding (phenylsulfonylmethyl)-triaryltin compound, (phenylsulfonylmethyl)triphenyltin, is formed when triphenyltin bromide is employed in the above Example in an equimolar amount in place of tributyltin chloride. The compound possesses bacteriostatic activity.

EXAMPLE IV

Using the apparatus and procedure of Example I, 100 ml. of an approximately one-molar solution of (p-methoxyphenylsulfonylmethyl)lithium in hexane-THF solvent was added dropwise with stirring to 0.1 mole of tributyltin chloride dissolved in THF. The temperature was maintained by means of an ice bath in the range of from 0° C to 10° C. Following the complete addition which required one-quarter hour, the reaction mixture was stirred for 2 hours at room temperature and hydrolyzed by pouring into aqueous one-molar ammonium chloride. Extraction from the hydrolyzate with ether solvent and purification by vacuum distillation yielded an odorless, pale-yellow liquid having a boiling point of 185° C/0.05 mm. Hg. The product was (p-methoxy-phenylsulfonyl-methyl)tributyltin. Infrared and proton nuclear magnetic resonance spectral analyses confirmed the assigned structure.

EXAMPLE V

Using the apparatus and procedure of Example I, 100 ml. of an approximately one-molar solution of (p-N,N-dimethylaminophenylsulfonylmethyl)-lithium in hexane-THF solvent was added dropwise with stirring to 0.1 mole of tributyltin chloride dissolved in THF. The temperature was maintained by means of an ice bath in the range of from −10° C to 20° C. Following the complete addition which required one-quarter hour, the reaction mixture was stirred for 2 hours at room temperature and hydrolyzed by pouring into aqueous one-molar ammonium chloride. Extraction from the hydrolyzate with ether solvent and purification by vacuum distillation yielded an odorless, pale-yellow liquid having a boiling point of 185°–190° C/0.05 mm. Hg. The product, (p-N,N-dimethylaminophenylsulfonylmethyl)tributyltin was analyzed and its assigned structure confirmed by proton nuclear magnetic resonance and infrared analyses.

EXAMPLE VI

Using the apparatus and procedure of Example I, 80 ml. of an approximately one-molar solution of (p-chlorophenylsulfonylmethyl)magnesium chloride in THF solvent was added (20° C) dropwise with stirring to 0.08 mole of tributyltin chloride dissolved in THF. Following the complete addition which required one-quarter hour, the reaction mixture was stirred for 1 hour at room temperature and hydrolyzed by pouring into aqueous one-molar ammonium chloride. Extraction from the hydrolyzate with ether solvent and purification by vacuum distillation yielded an odorless, pale-yellow liquid having a boiling point of 185°–190° C/0.07 mm. Hg. The product (p-chloro-phenylsulfonylmethyl)tributyltin was analyzed and gave 47.3% Carbon and 7.0% Hydrogen compared with the calculated values, respectively, of 47.5% and 6.9%. Infrared and proton nuclear magnetic resonance spectral analyses confirmed the assigned structure.

EXAMPLE VII

Using the apparatus and procedure of Example I, 50 ml. of an approximately one-molar solution of (o-methoxyphenylsulfonylmethyl)magnesium bromide in THF solvent was added (20° C) dropwise with stirring to 0.05 mole of tributyltin chloride dissolved in THF. Following the complete addition which required one-quarter hour, the reaction mixture was stirred for 16 hours at room temperature and hydrolyzed by pouring into aqueous one-molar ammonium chloride. Extraction from the hydrolyzate with ether solvent and purification by vacuum distillation yielded an odorless, pale-yellow liquid having a boiling point of 194°–195° C/0.07 mm. Hg. The product, (o-methoxyphenylsulfonylmethyl)tributyltin was analyzed and gave 50.1% Carbon and 7.7% Hydrogen compared with the calculated values, respectively, of 50.5% and 7.6%. Infrared and proton nuclear magnetic resonance spectral analyses confirmed the assigned structure.

Compounds of the invention have been tested as insecticides and as acaricides according to the following methods:

Insecticidal Evaluation Test: Four insect species as follows were subjected to evaluation tests for insecticidal properties:

I. Adult House Flies
II. Southern Armyworm Larvae
III. Mexican Bean Beetle Larvae
IV. Adult Pea Aphids The compounds of Examples I to IV, VI and VII were dissolved in acetone and dispersed in distilled water with Triton X-100 (iso-octyl phenyl polyethoxy ethanol) emulsifier. The samples were applied for a 10 second period to insects retained in a 2 inch × 5 inch diameter screened cage. The spray was applied from a Water's vertical spray tower operating at 10 p.s.i. and discharging about 30 ml. of material per minute through an atomizer. The spray descends through an 8 inch stainless steel cylinder to test insects below the atomizer. The insects were retained in the sprayed cages for mortality observations. In the case of House Fly treatment, 2-hour data represent knockdown; 24-hour data refer to mortality. The results are set forth in Table 1 below.

Table 1

| Compound | Conc. (W/V %) | Insect Mortality Tests | | | | |
|---|---|---|---|---|---|---|
| | | House 2 hr. | Flies 24 hr. | Armyworms 48 hr. | Bean Beetles 48 hr. | Aphids 48 hr. |
| Example I | 0.35 | 100 | 100 | 100 | 50 | 100 |
| | 0.10 | — | 5 | 75 | — | 100 |
| | 0.05 | — | 1 | 20(100) | — | 100 |
| | 0.01 | — | — | —(50) | — | 100(100) |
| | 0.005 | — | — | — | — | 25(90) |
| Example II | 0.35 | 100 | 100 | 100 | 70 | 100 |
| | 0.10 | — | 6 | 65 | — | 100 |
| | 0.05 | — | 2 | 10(100) | — | 100 |
| | 0.01 | — | — | — | — | 100(100) |
| | 0.005 | — | — | — | — | 10(90) |
| Example III | 0.35 | 0 | 62 | 100 | 90 | 100 |
| | 0.1 | — | — | 100 | 95 | 100 |
| | 0.05 | — | — | 90 | 70 | 100 |
| | 0.01 | — | — | 40 | 0 | 5 |
| Example IV | 0.35 | 0 | 0 | 100 | 80 | 100 |
| | 0.10 | — | — | 95 | 95 | 70 |
| | 0.05 | — | — | 55 | 45 | 50 |
| Example VI | 0.35 | 100 | 100 | 100 | 100 | 100 |
| | 0.10 | 0 | 0 | 95 | 75 | 75 |
| | 0.05 | — | — | 85 | 30 | 70 |
| | 0.01 | — | — | 15 | — | 25 |
| Example VII | 0.35 | 10 | 16 | 100 | 100 | 100 |
| | 0.10 | — | — | 85 | 0 | 50 |
| | 0.05 | — | — | — | — | — |

Numbers in parentheses refer to control compositions employed in a concentration of active equal to that of the weight/percent volume of the compounds of the invention. In the case of treatment of House Flies, the control compound was O,O-diethyl O-(2-isopropyl,4-methyl-6-pyrimidyl)phosphorothioate; the control for the Southern Armyworm and Mexican Bean Beetle larvae treatments was 1-naphthyl-N-methyl-carbamate; the control for the Pea Aphid treatment was S-[1,2-bis(ethoxycarbonyl)ethyl] 0-dimethyl phosphorodithioate.

As can be seen from the foregoing table, representative compounds of this invention possess excellent insecticidal properties. Particularly notable are the excellent mortality results in the case of the treatments of Southern Armyworm and Mexican Bean Beetle larvae and Pea Aphids. Effective knockdown and mortality characteristics are also evident from the treatment of House Flies with compounds of the invention.

Acaricidal Evaluation Test: The Strawberry Spider Mite was employed in tests for acaricidal activity. Bean seedlings were infested with approximately 100 mites. Dispersions of test compounds were prepared by dissolving the toxic material in acetone to provide a desired weight/volume percent. The solution was then diluted with water containing Triton X-100 emulsifier, the amount of water being sufficient to provide a stable emulsion. The test suspensions were sprayed on the infested bean seedlings. After 5 days, the plants were examined both for post-embryonic forms of the mites as well as eggs. The percentage of kill was determined on the basis of the original number of mites subjected to the treatment with the test suspensions. The acaricidal mortality is reported in Table 2.

Table 2

| Compound | % W/V | Strawberry Spider Mite Mortality % Mortality (5 days) |
|---|---|---|
| Example I | 0.35 | 100 |
| | 0.10 | 100 |
| | 0.05 | 100 |
| | 0.01 | 93(90) |
| | 0.005 | 56(62) |
| Example II | 0.35 | 100(100) |
| | 0.10 | 100 |
| | 0.05 | 100 |
| | 0.01 | 56(90) |
| | 0.005 | 15(62) |
| Example III | 0.35 | 100 |
| | 0.1 | 100 |
| | 0.05 | 100 |
| | 0.01 | 98(84) |
| | 0.005 | 97(79) |
| | 0.001 | 54(30) |
| Example IV | 0.35 | 100 |
| | 0.10 | 100 |
| | 0.05 | 100 |
| | 0.01 | 64(90) |
| | 0.005 | 35(72) |
| Example VI | 0.35 | 100 |
| | 0.10 | 100 |
| | 0.05 | 100 |
| | 0.01 | 100(95) |
| | 0.005 | 79(60) |
| | 0.001 | 22(8) |
| Example VII | 0.35 | 100 |
| | 0.10 | 100 |
| | 0.05 | 97 |
| | 0.01 | 79(95) |
| | 0.005 | 59(60) |

As can be seen from the acaricidal data, the compounds of the invention possess excellent acaricidal properties. Particularly evident are the excellent miticidal properties of a preferred compound, (phenyl-sulfonylmethyl)tributyltin. The miticidal properties of this compound compare favorably with those of a commercially available miticide, 4,4'-dichloro-alpha-trichloromethylbenzhydrol, employed on an equal concentration basis. 4,4'-dichloro-alpha-trichloro-methylbenzhydrol results are reported in parentheses in Table 2.

In addition to the excellent acaricidal activity of the compounds of the invention, the compounds of the invention have a toxicity to warm-blooded animals less than that of some important commercial insecticides. The oral $LD_{50}$ to rats of (phenyl-sulfonylmethyl)tributyltin, for example, is 400 mg./kg.

To determine the antibacterial activity of the compounds of the present invention, the following static test was employed. The species *Staphylococcus aureus*, a gram positive organism used for assaying bacteriostats and found on the skin of both man and lower animals, was employed. Compounds of the invention were added to the following matrices: FDA nutrient broth; FDA broth plus 25 ppm soap; and FDA broth plus 25 ppm synthetic detergent (commercially available formulation having an alkaryl sulfonate detergent active) at levels of 10, 2.5, 0.6 and 0.15 ppm. Four contact tubes were used for each dilution tested; three tubes were inoculated and the fourth was held as an uninoculated control. The FDA nutrient broth consisted of 5 grams Bacto Beef Extract, 10 grams Bacto Peptone and 5 grams C.P. grade NaCl in 1,000 ml. distilled water. The inoculum was a 24-hour broth culture of *Staphylococcus aureus* containing about 250 × $10^6$ organisms per ml. and was used in 0.1-ml. quantities. After inoculation, the tubes were shaken thoroughly, allowed to stand for 10 minutes for air bubbles to rise, and read for zero-hour turbidity value using a spectrophotometer at a setting of 610 m$\mu$. After 24 hours of incubation at 37° C the tubes were again shaken, allowed to stand 10 minutes, and read for 24-hour turbidity values. Differences in turbidity values are used as a measure of growth; the higher the value the more growth and the less effective is a material. No change in turbidity is evidence for antibacterial activity. The results reported in Table 3 are extrapolated breakpoints indicating the minimum concentration of bacteriostat required to inhibit *Staphylococcus aureus*.

Table 3

| | Static Test Against *Staphylococcus Aureus* | | | |
|---|---|---|---|---|
| | Nutrient Broth | | Matrix (25 ppm *S. aureus*) | |
| Compound | pH = 5.8 | pH = 6.8 | Soap | Synthetic Detergent Composition |
| Example I | > 10 ppm | > 10 ppm | > 10 ppm | > 10 ppm |
| Example II | > 10 | 2.5 | > 10 | 10 |
| Example III | 2.5 | 2.5 | 10 | 0.6 |
| Example VI | 10 | 10 | 10 | 2.5 |
| (phenylsulfonylmethyl)triphenyltin | > 10 | > 10 | > 10 | 0.6 |

As can be seen from the above data, the compounds of the invention possess bacteriostatic properties.

The fungicidal activity of the compounds of the present invention was evaluated as follows:

Compounds of the invention were dissolved in acetone at levels of 1000, 100 and 10 parts per million. One-half inch filter paper discs were saturated with the test solutions, dried and tested for antifungal activity by the Agar Plate Test, USDA Circular No. 198, 1931. All tests were performed upon Difco Sabouraud Dextrose Agar. All tests were incubated at 25° C, R.H. 96% for 5 days. Results for the compound of Example II are reported in Table 4 as follows: Results in parentheses represent those of a commercially available compound employed on an equal concentration basis, N-trichloromethylthio-4-cyclohexene-1,2-dicarboximide.

Table 4

| | Width of zone of inhibition in mm. | | |
|---|---|---|---|
| Test fungus | 1000 ppm | 100 ppm | 10 ppm |
| Candida albicans | trace | 0 | 0 |
| Trichophyton menta- grophytes | 8 | 4 | 0 |
| Glomerella cingulata | 5 | 3(11) | trace |
| Sclerotinia fructicola | 6 | 3(19) | trace |
| Aspergillus niger | 6 | 5(9) | 2 |
| Chaetomium globosum | 6 | 4 | 0 |

Results of antifungal testing of the compound of Example III are reported as follows in Table 5.

Table 5

| | Width of zone of inhibition in mm. | | |
|---|---|---|---|
| Test fungus | 1000 ppm | 100 ppm | 10 ppm |
| Candida albicans | trace | 0 | 0 |
| Trichophyton mentagrophytes | 3 | 2 | trace |
| Glomerella cingulata | 1 | trace | 0 |
| Sclerotinia fructicola | 3 | 1 | 0 |
| Aspergillus niger | 4 | 2 | trace |
| Chaetomium globosum | 2 | 0 | 0 |

As can be seen from the above data, the compounds (N,N-dimethylaminosulfonylmethyl)tributyltin and (phenylsulfonylmethyl)tributyltin possess fungicidal properties.

The novel compounds of the invention are useful for destroying a variety of pests. Accordingly, a method aspect of the present invention comprises combating pests by applying to a pest habitat one or more of the novel compounds of the invention. The compounds can be applied to a pest habitat or environment by application, in a pesticidally-active amount, to foliage, soil, barnyards, chicken pens, stables and other infected areas.

The organotin compounds herein are suitable for combating plant pests in the foregoing manner.

In accordance with the present invention, weeds (i.e., post-emergent control) or weed seeds (i.e., pre-emergent control) are contacted with an organotin compound of the type described herein in amounts sufficient to achieve the desired degree of weed control. The required dosage depends upon many factors such as method of application, type and quantity of weeds, duration of treatment, climatic conditions, etc. For example, growth suppression or wilting usually requires smaller dosages than does eradication. Application rates of from about 0.25 pounds to about 50 pounds of organotin compound per acre are usually satisfactory, but higher rates can also be used. Preferably the application rate is about 0.5 to 30 pounds per acre.

Any of the organotin compounds of the type herein disclosed are suitable for use as herbicides. Preferred for this use are those organotin compounds wherein the group A (in the general formula, above) is aryl, especially phenyl, and $R_2N$, wherein R is $C_1$ to $C_6$ alkyl, and wherein the group R' is $C_1$ to $C_6$ alkyl, especially butyl. (Phenylsulfonylmethyl)-tributyltin is especially preferred for use as a herbicide in the manner of this invention.

For practical use as herbicides, the organotin compounds herein are incorporated into herbicidal compositions comprising a plant-compatible carrier and an effective, i.e., growth controlling, amount of one or more of the organotin compounds. (As used herein a "plant-compatible" carrier is defined as an inert solvent or a dry bulking agent of the type hereinafter disclosed which has no substantial herbicidal effectiveness but which provides a means whereby the organotin compounds can be diluted for convenient application.) Such compositions can then be applied conveniently to the site of the weed infestation in any desired quantity. These compositions can be solids, such as dusts, granules or wettable powders, or they can be liquids such as solutions, aerosols, or emulsifiable concentrates. The solid compositions generally contain from about 1% to about 95% by weight of the organotin compounds and the liquid compositions generally contain from about 0.5% to about 70% by weight of said tin compounds.

Herbicidal Evaluation: (Phenylsulfonylmethyl)-tributyltin (prepared above) was screened for herbicidal activity on a variety of plants and plant pests including corn (*Zea mays*); soybeans (*Glycine max*); pigweed (*Amaranthus retroflexus*); wild mustard (*Brassica arvensis*); barnyard grass (*Echinachloa crusgalli*); and hairy crabgrass (*Digitaria sanguinallis*). The test seeds were planted in "Market-Pak" containers filled with about 1500 g. of a 2:1 mixture (wt.) of a silty loam top soil and a coarse quartz sand. The (phenylsulfonylmethyl)tributyltin was tested both for pre-emergent and post-emergent efficacy at an application rate of 10 pounds per acre (equivalent to ca. 0.037 g. of material per container, applied in ca. 5 ml. of acetone solvent containing 1% Tween 20). The solution was sprayed onto the soil surface (pre-emergence) and onto the plant (post-emergence) using an aerosol propellant power unit. Controls consisted of 3-amino-2,5-dichlorobenzoic acid ("Amiben") at 3 pounds per acre as a standard preemergence herbicide and 1,1-dimethyl-3-($\alpha,\alpha,\alpha$-trifluoro-m-tolyl)urea ("Fluormeturon") at 1.5 pounds per acre as the standard post-emergence herbicide. The compounds were graded on a scale of 0 to 10 with 0 being no effect on the plant (post-emergence) or no effect on plant growth (pre-emergence); 10 represents death (post-emergence) or no growth (pre-emergence). Results were as reported in Table 6.

Table 6

| Plant | Corn | Pig-Weed | Wild Mustard | Barnyard Grass | Hairy Crabgrass |
| --- | --- | --- | --- | --- | --- |
| Pre-emergent grade | 1 | 10 | 10 | 9 | 10 |
| Post-emergent grade | 4 | 10 | 10 | 10 | 10 |
| Amiben | 0 | 8 | 9 | 10 | 9 |
| Fluormeturon | 1 | 6 | 9 | 7 | 8 |

The above results clearly indicate the efficacy of (phenylsulfonylmethyl)tributyltin as a pre- and post-emergent herbicide on a variety of plant pests. The data also show the excellent selectivity of this organotin compound relative to corn. A non-toxic residue of tin oxide is left on the crops.

In the above procedure, the (phenylsulfonylmethyl)-tributyltin is replaced by an equivalent amount of (p-methoxyphenylsulfonylmethyl)tributyltin, (decylsulfonylmethyl)tributyltin, (phenylsulfonylmethyl)-triphenyltin, (N,N-dimethylaminosulfonylmethyl)-tributyltin, (naphthylsulfonylmethyl)tridecyltin, and (phenylsulfonylmethyl)tridecyltin and equivalent control, both pre- and post-emergent, of pigweed, wild mustard, barnyard grass and hairy crabgrass in the presence of corn and soybeans is secured. No toxic residues are left on the crops.

In the above procedure, the (phenylsulfonylmethyl)-tributyltin is applied broadcast to weed-infested growing alfalfa, oats and tomatoes at a rate of 5 pounds per acre and chickweed, cockleburr, lamb's quarters and foxtail are destroyed without substantial damage to the growing crops.

The organotin compounds herein are conveniently employed as pesticides in the form of solutions, emulsifiable concentrates, wettable powders, dusts, aerosols and the like. Suspensions or dispersions of the compounds of this invention in a non-solvent, such as water, are suitably employed in treating plant foliage. Also suitably employed are solutions of the insecticides, acaricides, herbicides, bacteriocides and fungicides of this invention in oil, and in oil which is emulsified in water. Examples of oil solvents include hydrocarbons such as benzene, toluene, kerosene and the like, and halogenated hydrocarbons such as chlorobenzene, chloroform, fluorotrichloro-methane and dichlorodifluoromethane.

Emulsifiers and wetting agents useful in the compositions herein are surface active agents of the anionic, nonionic (preferred), cationic, ampholytic and zwitterionic type and normally comprise from about 0.1% to 5% by weight of the concentrate. Examples of suitable anionic surface active agents are sodium salts of fatty alcohol sulfates having from 8–18 carbon atoms in the fatty chain and sodium salts alkyl benzene sulfonates, having from 9 to 15 carbon atoms in the alkyl chain. Examples of suitable nonionic surface active agents are the polyethylene oxide condensates of alkyl phenols, wherein the alkyl chain contains from about 6 to 12 carbon atoms and the amount of ethylene oxide condensed onto each mole of alkyl phenol is from about 5 to 25 moles. A preferred nonionic herein is the polyethylene oxide condensate of sorbitan mono-oleate (Tween). Examples of suitable cationic surface active agents are dimethyl dialkyl quaternary ammonium salts wherein the alkyl chains contain from about 8 to 18 carbon atoms and the salt forming anion is a halogen. Examples of suitable ampholytic surface active agents are derivatives of aliphatic secondary or tertiary amines in which one of the aliphatic substituents contains from about 8 to 18 carbon atoms and one contains an anionic water solubilizing groups, e.g., sulfate or sulfo. Specific suitable ampholytic surface active agents are sodium-3-dodecylaminopropionate and sodium-3-dodecyl amino propane sulfonate. Examples of suitable zwitterionic surface active agents are derivatives of aliphatic quaternary ammonium compounds in which one of the aliphatic constituents contains from about 8 to 18 carbon atoms and one contains an anionic water solubilizing group. Specific examples of zwitterionic surface active agents are 3-(N,N-dimethyl-N-hexadecylammonio)propane-1-sulfonate and 3-(N,N-dimethyl-N-hexadecylammonio)-2-hydroxy propane-1-sulfonate. Many other suitable surface active agents are described in "Detergents and Emulsifiers — 1969 Annual", by John McCutcheon, Inc., which is incorporated herein by reference.

Aerosols prepared by dissolving the compounds of this invention in a highly volatile liquid carrier such as trifluorochloromethane, nitromethane, and the like, or by dissolving such compounds in a less volatile solvent, such as benzene, and admixing the resulting solution with a highly volatile liquid aerosol carrier, can also be employed to advantage.

The liquid and aerosol compositions herein can contain up to about 70% (wt.) of the organotin compounds; concentrations of about 1% to 10% (wt.) are suitable for most purposes.

Compositions in the form of dusts can be prepared by admixing the compounds of the invention with dry free-flowing powders such as clay, bentonite, fuller's earth, diatomaceous earth, pyrophyllite, attapulgite, calcium carbonate, chalk or the like. Wettable dusts also include from about 0.1% to 5% by weight of one or more of the surface-active agents described above. The active compounds of the invention normally comprise up to about 70% by weight of such dust formulations. An amount of up to about 5% is preferred and is suitable for most applications.

What is claimed is:
1. A method of combatting undesirable vegetation which comprises applying thereto an herbicidally effective amount of a compound of the formula

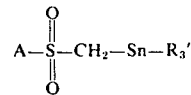

where A is alkyl of from 1 to 14 carbon atoms; hydrocarbyl aryl; chloro, diloweralkylamino or methoxy substituted hydrocarbyl aryl; $R_2N-$, where R is alkyl of from 1 to 14 carbon atoms; and each R' is alkyl of from 1 to 14 carbon atoms or hydrocarbyl aryl.

2. The method of claim 1 wherein A is alkyl of from 1 to 14 carbon atoms.
3. The method of claim 2 wherein A is butyl.
4. The method of claim 3 wherein each R' is butyl.
5. The method of claim 1 wherein A is aryl.
6. The method of claim 5 wherein A is phenyl.
7. The method of claim 6 wherein each R' is butyl.
8. The method of claim 1 wherein A is substituted aryl and each R' is butyl.
9. The method of claim 1 wherein A is $R_2N-$, where each R is methyl; and each R' is butyl.
10. The method of claim 1 wherein the compound is (phenylsulfonylmethyl)trihexyltin.
11. The method of claim 1 wherein A is $R_2N-$, where each R is methyl; and each R' is hexyl.

* * * * *